United States Patent [19]
Lancee et al.

[11] Patent Number: 5,375,602
[45] Date of Patent: * Dec. 27, 1994

[54] ULTRASONIC INSTRUMENT WITH A MICRO MOTOR

[75] Inventors: Charles T. Lancee, Waarder; Nicolaas Bom, Berkenwoude, both of Netherlands

[73] Assignee: Du-Med, B.V., Rotterdam, Netherlands

[*] Notice: The portion of the term of this patent subsequent to Aug. 31, 2010 has been disclaimed.

[21] Appl. No.: 113,721

[22] Filed: Aug. 27, 1993

Related U.S. Application Data

[63] Continuation of Ser. No. 820,571, Jan. 14, 1992, Pat. No. 5,240,003, which is a continuation-in-part of Ser. No. 765,084, Sep. 24, 1991, abandoned, which is a continuation-in-part of Ser. No. 591,652, Oct. 2, 1990, Pat. No. 5,176,141.

[51] Int. Cl.$^5$ .................................................. A61B 8/12
[52] U.S. Cl. .................................................. 128/662.06
[58] Field of Search ...................... 128/660.1, 662.06; 310/40 MM, 156, 162, 184, DIG. 6

[56] References Cited

U.S. PATENT DOCUMENTS

| | | | |
|---|---|---|---|
| 4,546,771 | 10/1985 | Eggleton et al. | 128/600 |
| 4,644,246 | 2/1987 | Knapen | 320/21 |
| 4,794,931 | 1/1989 | Yock | 128/660.03 |
| 4,908,808 | 3/1990 | Knapen et al. | 368/157 |
| 4,917,096 | 4/1990 | Englehart et al. | 128/660.1 |
| 4,924,869 | 5/1990 | Takeuchi et al. | 128/660.05 |
| 5,000,185 | 3/1991 | Yock | 128/662.03 |
| 5,010,886 | 4/1991 | Passafaro et al. | 128/660.03 |
| 5,024,234 | 6/1991 | Leary et al. | 128/663.01 |
| 5,029,588 | 7/1991 | Yock et al. | 128/662.06 |
| 5,059,851 | 10/1991 | Corl et al. | 310/334 |
| 5,061,273 | 10/1991 | Yock | 606/194 |
| 5,095,911 | 3/1992 | Pomeranz | 128/662.06 |
| 5,176,141 | 1/1993 | Bom et al. | 128/662.06 |
| 5,240,003 | 8/1993 | Lancee et al. | 128/662.06 |

FOREIGN PATENT DOCUMENTS

3219118A1 12/1982 Germany.

OTHER PUBLICATIONS

"Early and recent intraluminal ultrasound devices", *International Journal of Cardiac Imaging*, vol. 4, 1989, pp. 79–88.

Primary Examiner—Francis Jaworski
Attorney, Agent, or Firm—Thomas R. Vigil

[57] ABSTRACT

The disposable intra-luminal ultrasonic instrument comprises: a catheter having an elongate axis and a hollow distal end portion; an acoustical mirror face; structure for mounting the acoustical mirror face for rotation in the distal end portion of the catheter with the acoustical mirror face arranged at an angle to the elongate axis of the catheter; a transducer; structure for mounting the transducer in the distal end portion of the catheter in a position to propagate acoustic waves toward the acoustical mirror face; a micromotor having a length no greater than approximately 6 millimeters and a diameter no greater than approximately 2.4 millimeters; structure for mounting the micromotor in the distal end portion of the catheter; structure for connecting the micromotor to the acoustical mirror face; conductors for connecting the micromotor to a source of energy for energizing the micromotor to rotate the acoustical mirror face; and, conductors for connecting the transducer to a source of energy for energizing the transducer to produce and supply sound waves to the rotatable acoustical mirror face.

18 Claims, 6 Drawing Sheets

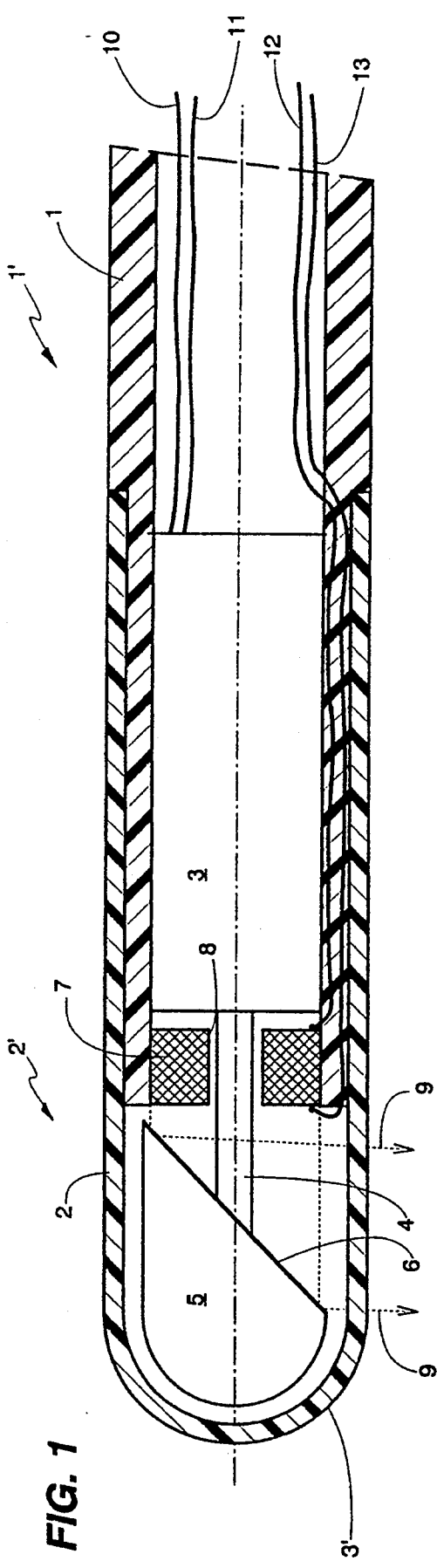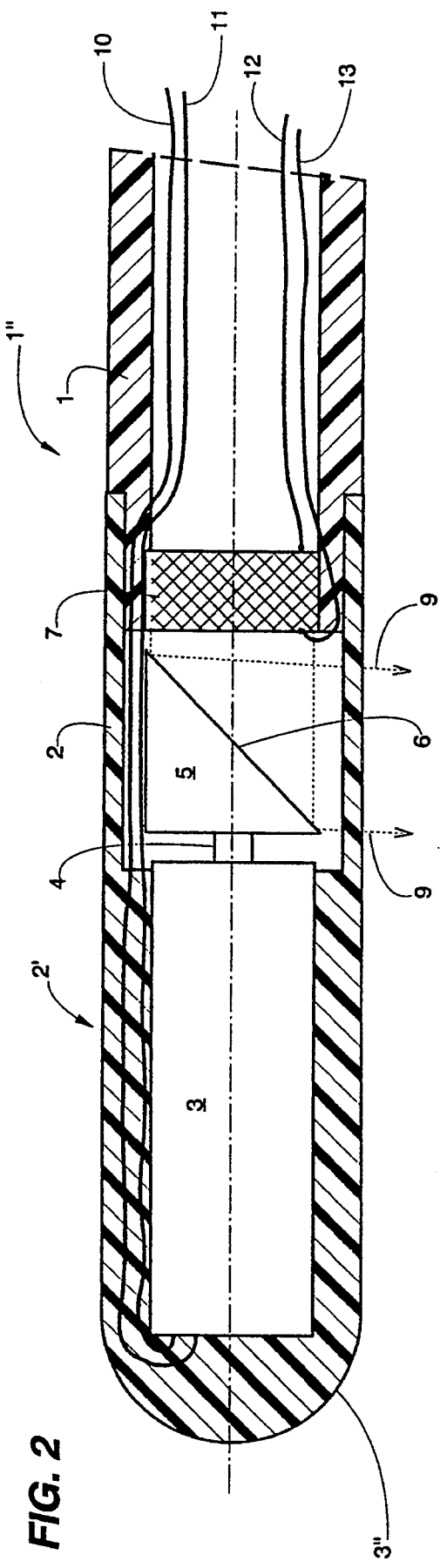

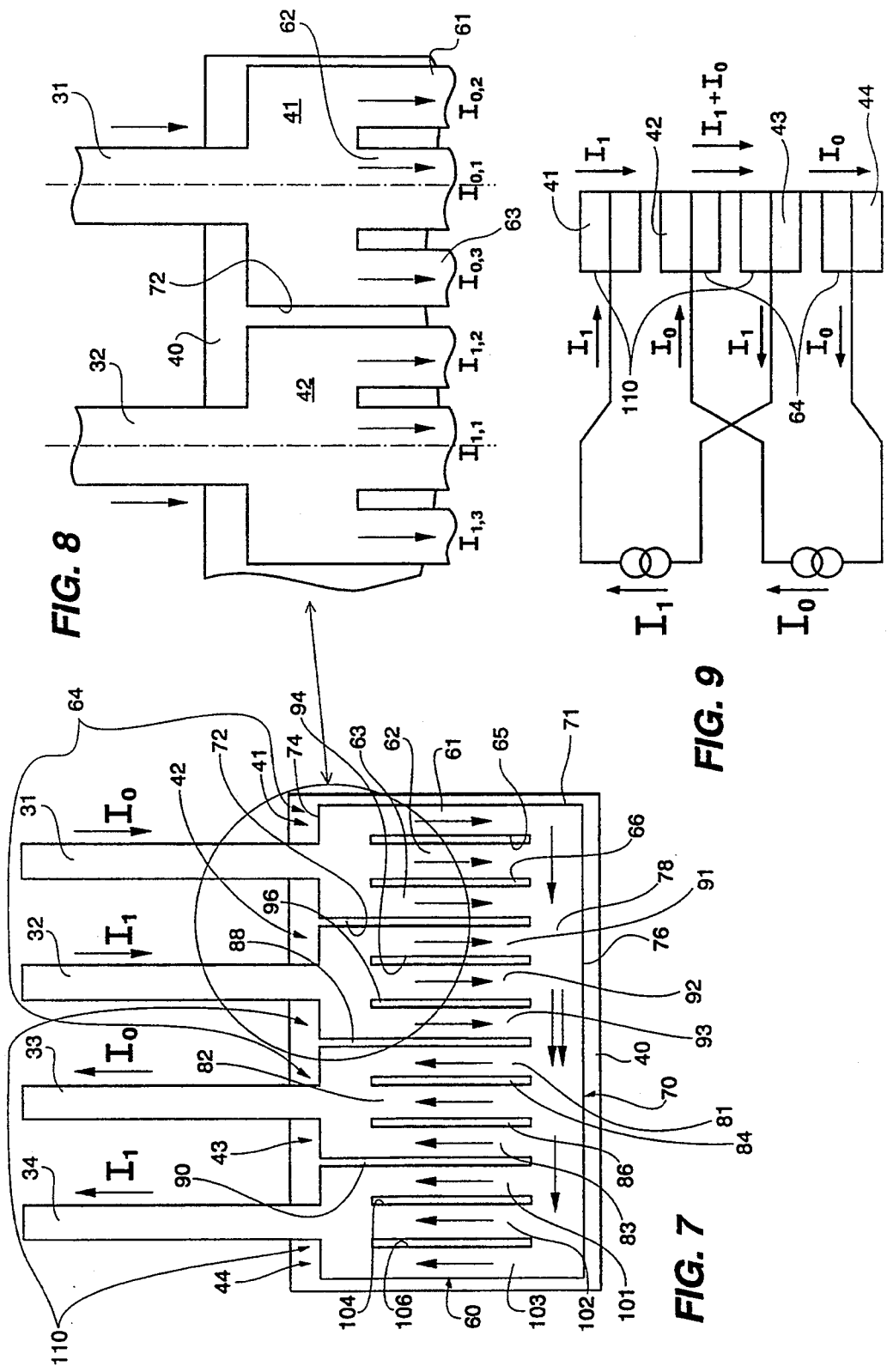

ULTRASONIC INSTRUMENT WITH A MICRO MOTOR

CROSS-REFERENCE TO RELATED APPLICATIONS

This application is a continuation of U.S. patent application Ser. No. 07/820,571 filed Jan. 14, 1992 for: ULTRASONIC INSTRUMENT WITH A MICRO MOTOR HAVING STATOR COILS ON A FLEXIBLE CIRCUIT BOARD, now U.S. Pat. No. 5,240,003 issued on Aug. 31, 1993 which is a continuation-in-part of U.S. patent application Ser. No. 07/765,084 filed Sep. 24, 1991 for: ULTRASONIC INSTRUMENT WITH A MICRO MOTOR HAVING STATOR COILS ON A FLEXIBLE CIRCUIT BOARD, now abandoned, which is a continuation-in-part of U.S. patent application Ser. No. 07/591,652 filed Oct. 2, 1990 for: A DISPOSABLE INTRALUMINAL ULTRASONIC INSTRUMENT, now U.S. Pat. No. 5,176,141 issued on Jan. 5, 1993.

BACKGROUND OF THE INVENTION

1. Field of the Invention

The present invention relates to a disposable intraluminal ultrasonic instrument which includes a catheter that has an ulterasonic sound wave transducer therein and a rotatable acoustic mirror for directing the sound waves outwardly into tissue and for receiving echo sounds and directing the echo sounds to the transducer for transmission to a visual display which displays an ultrasound picture of the tissue whereby one can determine the makeup or construction of the tissue, e.g., hard or soft. The present invention also relates to a micro motor used in such an instrument for rotating the acoustic mirror while the transducer provides sound waves to the acoustic mirror.

2. Description of the related art including information disclosed under 37 CFR Sections 1,97-1.99

Heretofore it has been proposed in Dutch Patent Application No. 87.00632 to provide a catheter having a catheter tip with a rotatable acoustic mirror therein or a rotatable tip having an acoustic mirror therein. A flexible shaft extends from the rotatable acoustic mirror to the proximal end of the catheter where it is driven by a suitable motor situated outside the catheter. A transducer is mounted in the catheter tip opposite the rotatable acoustic mirror. Rotation of the acoustic mirror within the tip of the tip portion having the mirror thereon causes high frequency ultrasonic vibrations or sound waves emitted by the transducer to be emitted in different directions in a rotating path and the echoes of the sound waves are received by the acoustic mirror and thence by the transducer for transmission to a visual display whereby a picture can be created cf the space around the catheter tip which may contain tissue or a stenotic buildup in a vessel.

A problem with the instrument having the catheter described above is that the flexible drive shaft is fairly long, i.e., at least as long as the catheter itself. With this arrangement, it is difficult to supply a torsion free rotational force through the flexible drive shaft and to drive such a long flexible drive shaft for extended periods of time without malfunctioning.

As will be described in greater detail below, the present invention provides an intra-luminal ultrasonic instrument which does not have the problem of a long drive shaft by providing a micro motor of very small diameter in the catheter tip for driving a short drive shaft coupled to an acoustic mirror in the catheter tip, the motor having flat stator coils mounted on a flexible circuit board.

It has been suggested in Dutch Patent Application No. 87.00632 to provide a turbine driven by fluid at or near the catheter tip with the turbine having a short drive shaft coupled to the rotatable acoustic mirror.

Heretofore it has been proposed in European Patent Application Publication No. 0 139 574 to provide an endocavity probe having a motor mounted in the distal end of one embodiment of the probe. The motor rotates a mirror which reflects signals emitted by a transducer.

This probe is utilized in examining organs and the like of a body. The probe is somewhat bulky in shape any size, is intended for insertion in body cavities, is not suitable for insertion inside veins and/or arteries and does not teach a motor having stator coils mounted on a flexible circuit board and having a diameter no greater than 3 millimeters mounted in a catheter tip.

In the Sakai German Offenlegungsschrift DE 32 19 118 A1 there is disclosed an endoscope having a metal housing in which is mounted a rotatable mirror and a motor for rotating the mirror. Also, fiber optics are provided for viewing capabilities. This patent publication does not disclose or suggest a catheter tip no greater than 3 millimeters in diameter having a micro motor mounted therein for rotating an acoustic mirror positioned adjacent to a transducer in the catheter tip.

The Eggleton et al. U.S. Pat. No. 4,546,771 discloses an acoustic microscope which has a transducer capable of producing and receiving high frequency acoustical beams and is positioned within a needle. This patent teaches using frequencies of 100 megahertz to 400 megahertz, and preferably frequencies of 500 megahertz or greater. These frequencies do not produce the necessary depth obtained with frequencies under 60 megahertz as utilized in the ultrasonic instrument of the present invention.

This patent teaches the rotation of a rotating member by an arrangement of small electromagnets and permanent magnets attached to a needle. The needle in this patent can only be inserted into tissue for biopsy procedures and is not adapted to be inserted into a blood vessel, nor is it intended to be inserted into a blood vessel like the catheter tip of the present invention for evaluating space around the catheter tip and particularly, the tissue or stenotic buildup located around the catheter tip to a sufficient depth.

A number of ultrasonic instruments for the examination and/or treatment of blood vessels have been previously proposed. Examples of these previously proposed instruments are disclosed in the following United States Patents, the disclosures of which are incorporated herein by reference:

| Patentee | U.S. Pat. No. |
| --- | --- |
| Yock | 4,794,931 |
| Pope et al | 4,889,757 |
| Prodian et al | 4,917,097 |
| Yock | 5,000,185 |
| Lum et al | 5,003,238 |
| Passafaro | 5,010,886 |
| Yock et al | 5,029,588 |

A miniature stepper motor for use in timepiece is disclosed in the Knapen et al U.S. Pat. No. 4,908,808 assigned to Kinetron, B.V., The Netherlands.

According to the present invention there is provided a disposable intra-luminal ultrasonic instrument comprising: a catheter having an elongate axis and a hollow distal end portion; an acoustical mirror face; structure for mounting the acoustical mirror face for rotation in the distal end portion of the catheter with the acoustical mirror face arranged at an angle to the elongate axis of the catheter; a transducer; structure for mounting the transducer in the distal end portion of the catheter in a position to propagate acoustic waves toward the acoustical mirror face; a micromotor having a length no greater than approximately 6 millimeters and a diameter no greater than approximately 2.4 millimeters; structure for mounting the micromotor in the distal end portion of the catheter; structure for connecting the micromotor to the acoustical mirror face; conductors for connecting the micromotor to a source of energy for energizing the micromotor to rotate the acoustical mirror face; and, conductors for connecting the transducer to a source of energy for energizing the transducer to produce and supply sound waves to the rotatable acoustical mirror face.

BRIEF DESCRIPTION OF THE DRAWINGS

FIG. 1 is a cross-sectional view of a catheter tip of one embodiment of the disposable intra-luminal ultrasonic instrument constructed according to the teachings of the present invention.

FIG. 2 is a cross-sectional view of a catheter tip, similar to the view shown in FIG. 1, of another disposable intra-luminal ultrasonic instrument constructed according to the teachings of the present invention.

FIG. 7 is a plan view of the flexible circuit board with the flat frame stator coils mounted thereon before it is folded into a cylindrical shape, as shown in FIG. 4.

FIG. 8 is an enlarged fragmentary view, with portions broken away, of a portion of the circuit board and flat stator frame coils thereon shown in FIG. 7.

FIG. 9 is an equivalent circuit diagram of the electrical circuit of the stator coils shown in FIG. 7.

DESCRIPTION OF THE PREFERRED EMBODIMENT(S)

Figure 3:
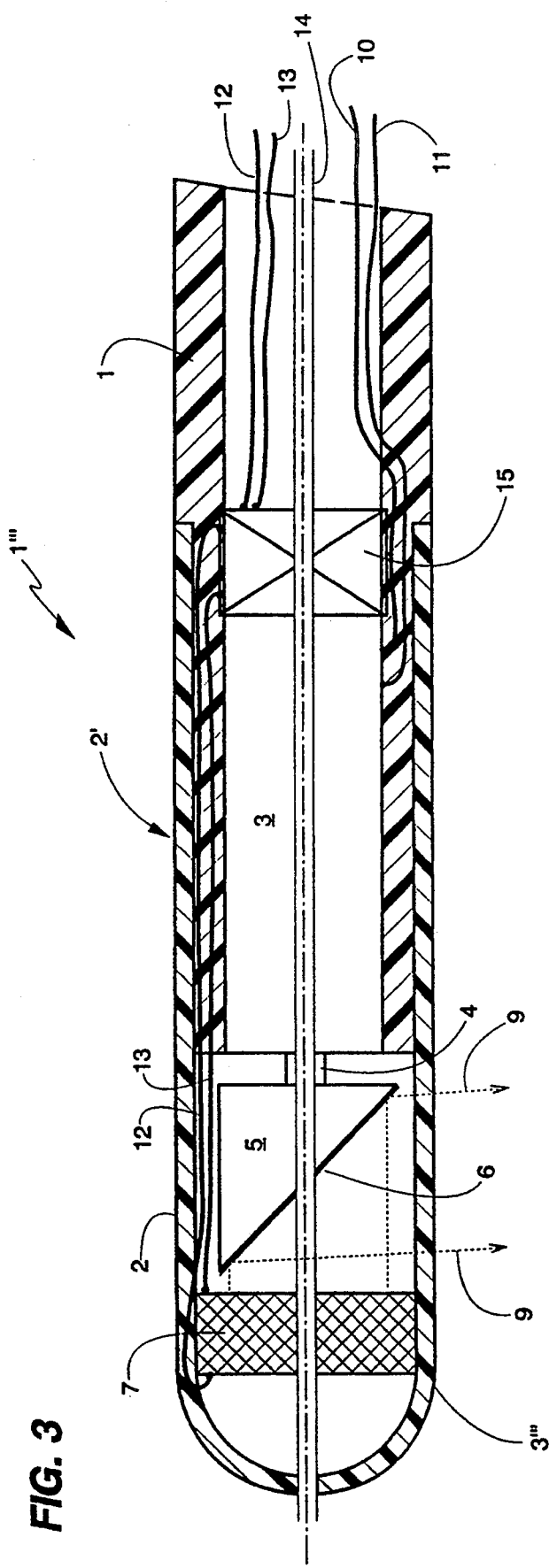
FIG. 3 is a cross-sectional view of a catheter tip, similar to the view shown in FIG. 1, of still another disposable intra-luminal ultrasonic instrument constructed according to the teachings of the present invention.

Referring now to the Figures in greater detail, there is illustrated in FIG. 1 a catheter 1 in the form of a thin flexible tube made of a suitable disposable material, e.g., a plastic material which forms part of a disposable intra-luminal ultrasonic instrument 1'. The outer of the tube 1 is not more than 2.7 millimeters and will be 0.62 millimeters, if the instrument is used for the examination and/or treatment of coronary vessels.

A small cap 2 of a suitable material, e.g., a plastic material, is fastened onto a distal end portion of the flexible tube 1 to define a catheter tip 2'. The cap 2 is made of a material which is transparent to ultrasonic radiation or sound waves when the instrument is provided with means for emitting ultrasonic radiation and for receiving the echoes of the emitted radiation. In any event, the cap 2 has a window for allowing this ultrasonic radiation to pass through the cap 2.

A cylindrical micro 3 is fastened in the distal end portion of the flexible tube 1 near the distal end cf the tube 1 with the motor 3 being substantially co-axial with the axis of the catheter tube 1.

In this embodiment of the instrument 1', the motor 3 is placed at some distance from the distal end of the catheter tip 2'.

A drive shaft 4 extends distally from, is part of, and is driven by the motor 3.

A rotatable element, which in this embodiment of the instrument 1' is a rotatable acoustic mirror 5, is mounted on the drive shaft 4 and has a mirror face 6 which lies in a plane that intersects the axis of the catheter tube 1 at an angle, as well as intersecting the axis of the drive shaft 4 of the motor 5. The mirror 5 is rotatable with and on the drive shaft 4 during operation of the motor 3.

The motor 3 can be driven at an rpm between 600 and 4,000 rpm, e.g., 1,200 rpm, 1,800 rpm, 3,000 rpm or 3,600 rpm up to but not limited to 6,000 rpm.

The rotational speed of the motor is correlated with a raster across a visual display (not shown) which is connected to the instrument 1'

A transducer 7 is mounted within the distal end portion of the catheter tube 1 between the motor 3 and the mirror face 6 opposite or facing the mirror 6.

As shown, the transducer 7 has a central passageway or channel 8 therethrough through which the drive shaft 4 extends.

Ultrasonic radiation at critically selected frequencies is emitted by the transducer 7 at the mirror face 6 and reflected outwardly by the mirror face 6 in the direction generally driven by the arrows 9. This reflected bundle of radiation waves 9 emerges from the catheter tip 2' via a window formed in or defined by the cap 2.

If the ultrasound wave is reflected by an obstacle, such as an artery wall, when the catheter tip is mounted in an artery, the reflected or echoed signal so generated will pass through the window, impinge upon the mirror face 6 and will be reflected to and received by the transducer 7. The reflected sound waves are then supplied by the transducer 7 to a visual display where an ultrasound image of the space surrounding the catheter tip 2′ and the material in that space can be displayed on a visual display, the raster of which is coordinated with the speed of rotation of the acoustic mirror 5. The operating frequency of the sound wave will determine the depth of field of this ultrasonic imaging.

It has been found that in the megahertz frequency range lower frequencies, e.g., below 10 megahertz, will provide a deeper depth of field but with low resolution which might not be satisfactory. On the other hand, it has been found that frequencies between 45 and 60 megahertz, while providing good resolution, result in a shallower depth of field. Accordingly, in the instrument 1′ of the present invention the ultrasonic sound waves generated by the transducer 7 are generated by a frequency that is not greater than 60 megahertz typically in the range of 15 and 45 megahertz, and preferably at approximately 30 megahertz for a good balance between depth of field and resolution.

The manner in which ultrasonic pictures can be formed of the space surrounding the catheter tip 2′ with the aid of echoes or ultrasonic radiation is described in Dutch Patent Application No. 87.00632, the disclosure of which is incorporated herein by reference.

The motor 3 is preferably a synchronous motor. The power supply for the motor 3 can be outside the catheter tube 1 with the motor 3 being coupled to the power supply by a plurality of electrical wire conductors 10 and 11. These wire conductors 10 and 11 extend through the interior of the catheter tube 1 between the power supply and the motor 3 to which they are connected. The wire conductors 10 can be a plurality of current supply wires 10 and the wire conductors 11 can be a plurality of current removal, ground or common, wires 11.

Also, electrical wire conductors 12 and 13 for transmitting the electrical signals to and from the transducer 7 are received within and extend within catheter tube 1 between the transducer 7 on the distal end of the wire conductors 12 and 13 to an external drive and visual drive at the proximal drive of the wire conductors 12 and 13.

In the embodiment of the disposable ultra-luminal ultrasonic instrument 1″, shown in FIG. 2, the motor 3 is mounted in the outer distal end portion 3″ of the cap 2. In this embodiment, the drive shaft 4 extends proximally from the motor 3 and has the mirror 5 with mirror face 6 mounted thereon. The transducer 7 is then mounted proximally of the mirror 5 opposite or facing the mirror face 6 within the flexible catheter tube 1 at the distal end thereof.

It will be appreciated that the end cap 2 and motor 3 can be constructed as an integral unit and then mounted on the distal end of the flexible catheter tube 1 with the peripheral area of the cap 2 surrounding the mirror face 6 being of reduced thickness to enable the bundle of ultrasonic waves 9 reflected by the mirror face 6 to pass through the thin wall of the cap 2 and then permit reflected sound waves or echoes to come back through the thin wall of the cap 2. The electrical wire conductors 10 and 11 for the motor 3 and the electrical wire conductors 12 and 13 for the transducer 7 again extend through the interior of the catheter tube 1, as in the embodiment of the instrument 1′ shown in FIG. 1.

Referring now to FIG. 3, there is illustrated therein still another embodiment 1‴ of the disposable intraluminal ultrasonic instrument of the present invention. In this embodiment, the instrument 1‴ has the transducer 7 mounted in a distal end portion 3‴ of the cap 2. The motor 3 is then mounted in the distal end portion of the catheter tube 1 much the same way as in the embodiment of the instrument 1′ in FIG. 1. Then, the mirror 5 with a mirror face 6, similar to the mirror 5 shown in FIG. 2, is mounted between the transducer 7 and the motor 3 with the mirror face 6 facing the transducer 7 and the acoustic mirror 5 mounted on the drive shaft 4 of the motor 3.

Thus, in FIGS. 1 and 2, the mirror face 6 faces proximally of the catheter tip 2″, and in FIG. 3 the mirror face 6 faces distally of the catheter tip 2″.

Also, in the instrument 1‴ shown in FIG. 3, a capillary tube 14 extends through suitable aligned bores in the motor 3, the drive shaft 4, the mirror 5, the transducer 7 and the distal end of the distal end portion 3″40 of the cap 2.

With this construction of the instrument 1‴ a guidewire can be inserted through the catheter tube 1, namely through the capillary tube 14 and protrude beyond the distal end of the distal end portion 3‴ of the cap 2 for various known catheter procedures.

If desired, an electronics switch 15, such as an integrated circuit switch, which includes circuitry for amplifying the reflected or echoed signal received by the transducer 7 before such signal is transmitted via the wire conductors 12 and 13 to the visual display can be provided.

Furthermore, the wire conductors 10 and 11 to the motor 3 and/or the wire conductors 12 and 13 to the transducer 7 can be used jointly as means for determining the position of a catheter in a lumen, i.e., to determine the relative position of a catheter tip 2 with respect to the surrounding space.

In the instrument 1′ shown in FIG. 1, the wire conductors 12 and 13 extend from the transducer 7 through, or are embedded in, the distal end portion of the catheter tube 1 and the wire conductors 10 and 11 extend proximally from the motor 3.

In the instrument 1″ shown in FIG. 2, the wire conductors 10 and 11 are fixed in place in the distal end portion 3″ of the catheter tip 2 and extend across or intersect the path of the emitted and reflected sound waves 9 and then through the distal end portion of the catheter tip portion 1 to the interior of the catheter tube 1. Thus, the portion of the wire conductors 10 and 11 in the vicinity of the mirror 5 will be seen on the visual display so that the position of the catheter tip relative to the area of the lumen or blood vessel under investigation can be determined.

Likewise, the position of a portion of the wires 12 and 13 extending within the cap 2 in the vicinity of the mirror 5 can be seen on the visual display for determining the orientation and location of the catheter tip 2″ relative to the area of the lumen or blood vessel under investigation.

This orientation method is comparable to the orientation method described in Dutch Patent Application No. 89.01084, the disclosure of which is incorporated herein by reference.

From the foregoing description of the embodiments 1′, 1″. 1‴ shown in FIGS. 1–3, the positions, respectively, of the motor 3, the mirror 5 and the transducer 7 can be adjusted as desired.

The mirror face 6 is angled to the catheter axis in a manner as taught in Dutch Patent Application No. 87.00632.

In the embodiment shown in FIG. 1, the transducer 7 has a central channel 8 through which the drive shaft 4 can extend.

The motor 3 of the intra-luminal ultrasonic instrument 1', 1" or 1'" is substantially cylindrical and has a length of less than approximately 6 millimeters, and a diameter of not more than approximately 2.4 millimeters, preferably not more than approximately 1 millimeter.

Also, as described above, devices such as the electrical wire conductors and their position can be utilized for determining the orientation of the catheter tip with respect to the surrounding space as taught in Dutch Patent Application No. 89.01084.

The instrument 1', 1" or 1'" can be fitted in a suitable manner with devices to perform an examination inside the artery or vein after the examination has taken place, or even during the examination, to use an obstructive method, for example, for destroying plaque.

The instrument 1', 1" or 1'" can, for example, be fitted with devices to perform the spark erosion method, as described in the Dutch Patent Application No. 87.00632.

It is also possible to provide the instrument 1', 1" or 1'" with a balloon for use in a balloon dilatation method which is well known in the field of angioplasty. In the practice of an angioplasty method, a suitable balloon can be fastened around the catheter tip 2', 2" or 2'" and a separate channel can be built in along the catheter tube 1 which is connected to the balloon for inflating it while operating it and thereafter allowing the balloon to deflate.

As described in connection with the description of FIG. 3, a central channel or capillary tube 14 can be provided for receiving a guidewire through the catheter tube 1 and the catheter tip 2'".

The space in the catheter tip 2', 2", 2'" where the transducer 7 and mirror tip 5 are located is primarily filled with a liquid before operating the instrument 1', 1" or 1'" to ensure efficient acoustical operation of the instrument 1', 1" or 1'". The above referred to space can be pre-evacuated using vacuum techniques and liquid can be sucked into the space via suitable channels. It is also possible to directly introduce liquid into the space via a filling tube so that the air or other gas present is expelled via suitable degassing channels in the catheter tube 1. The filling tube can be a separate lumen in the catheter tube 1 or can be a small tube fitted along or in the catheter tube 1 itself and which can be pulled away after use.

Furthermore, if desired, the integrated switch 15, as shown in FIG. 3, can be mounted in the catheter tip 2" of the instrument 1', 1" or 1'" adjacent the motor 3 and the transducer 7. This structural arrangement can be provided to assist in the amplification of the echo signal emitted by the transducer 7 before it is transmitted by the wire conductors 12 and 13 to the visual display; and such amplification allows certain, structure in or on the catheter tube 1 to be omitted, e.g., the provision of a metal wire integrated with the catheter mantle, and working as a Faraday's cage, and concealed within the catheter tube 1 can be omitted.

The instrument 1', 1" or 1"40 works well with a French 5 catheter having a diameter of approximately 1.6 millimeters.

Furthermore, the transducer 7 is constructed, arranged and operated to emit sound waves at no more than 60 megahertz, typically somewhere between 15 and 45 megahertz, and in one preferred use of the instrument 1', 1" or 1'", at approximately 30 megahertz.

It has been found that the frequencies used, particularly approximately 30 megahertz, results in an ultrasound picture having a depth of field of at least one-half inch ($\frac{1}{2}$") with good resolution so that the makeup or constitution, e.g., hard calcified or soft fatting material, of the tissue or stenotic buildup being investigated can be determined. Furthermore, the instruments 1', 1" or 1'" having the constructions described above with reference to FIGS. 1-3, are constructed in a simple and inexpensive manner which allows the instrument 1', 1" or 1"40 to be a disposable instrument.

Figure 4:
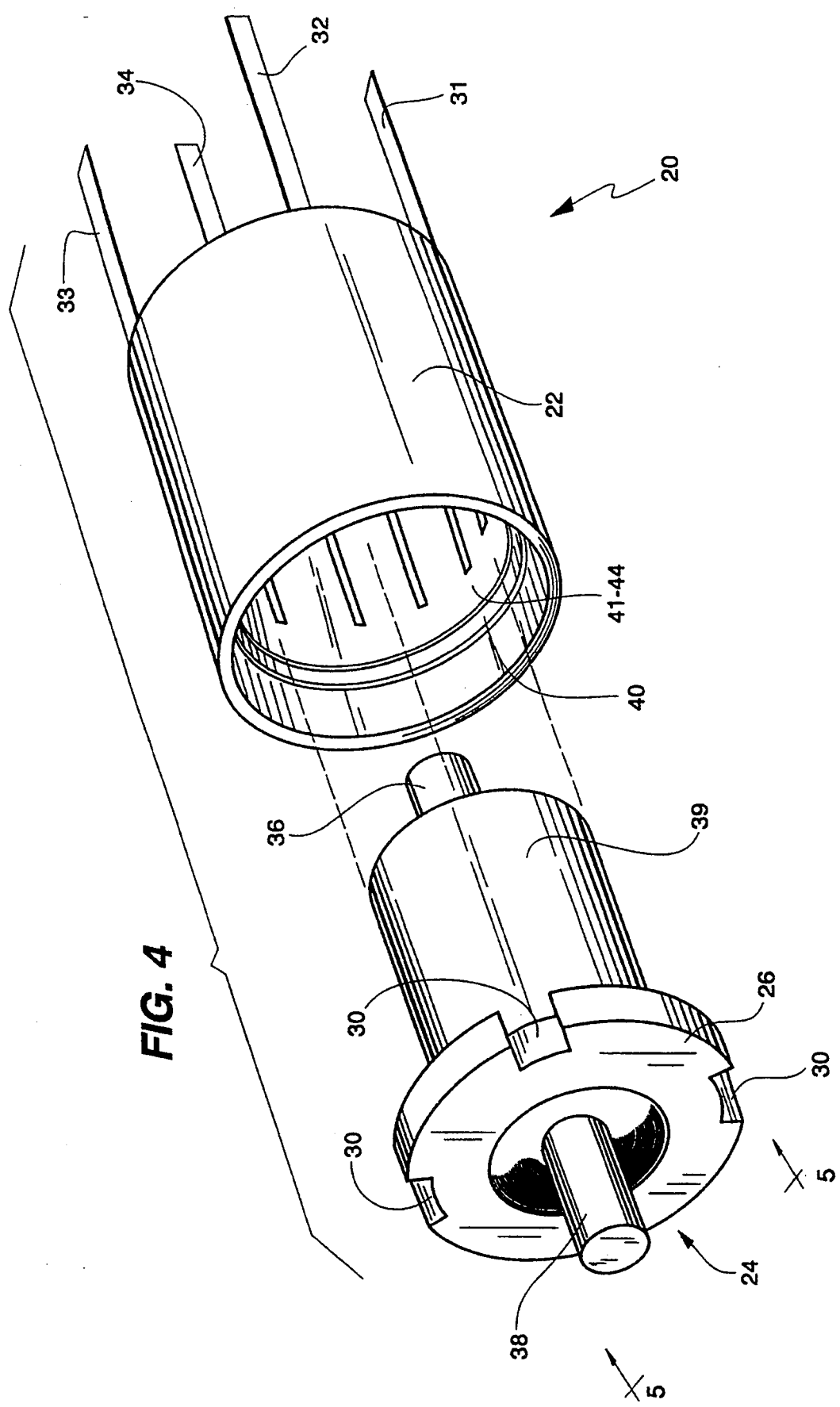
FIG. 4 is an exploded perspective view of a micro motor constructed according to the teachings of the present invention and having flat stator coils mounted on a flexible circuit board which is folded to a cylindrical shape.
Figure 5:
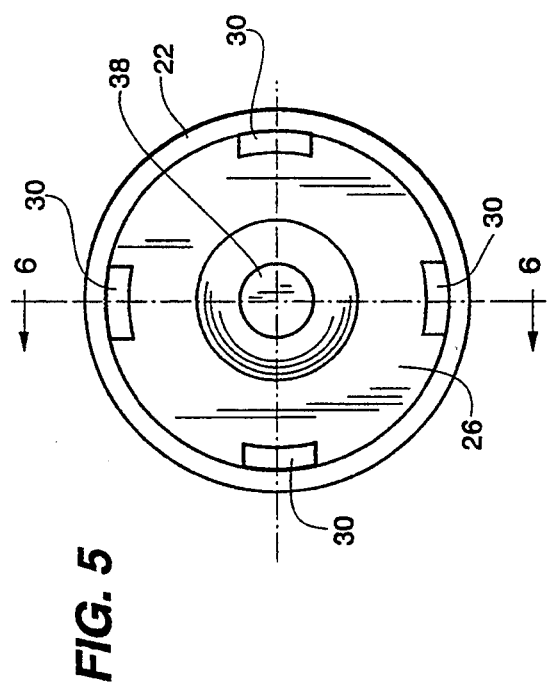
FIG. 5 is an end view of the micro motor showing the output shaft end of the motor.
Figure 6:
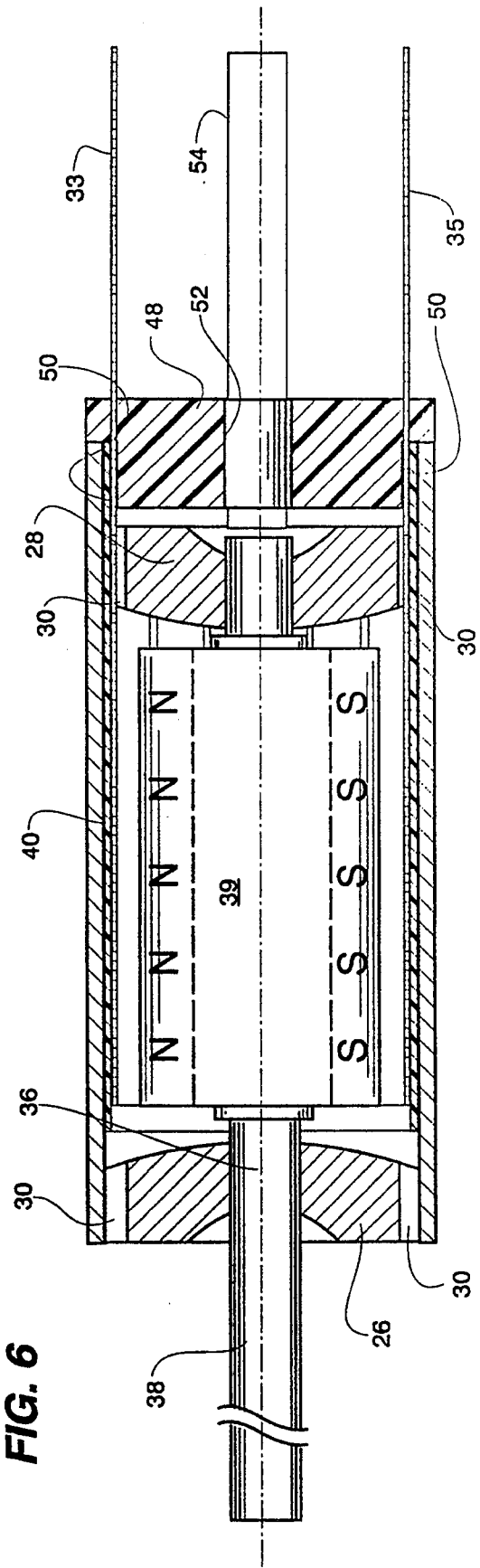
FIG. 6 is a longitudinal sectional view of the micro motor and is taken along line 6—6 of FIG. 5.

In FIGS. 4-6 there is illustrated a micro motor 20 that is a flex print micro motor 20 particularly adapted for use in the intra-luminal ultrasonic instrument 1, 1', 1" or 1'" shown in FIGS. 1-3. As shown in FIGS. 4-6, the flex print micro motor 20 includes a non-magnetic stator shell or housing 22. Mounted at one end, and typically the distal end 24 of the motor 20, is a first bearing 26 and within the stator housing 22 is mounted a similar second bearing 28 (FIG. 6). Each of the bearings 26 and 28 has four side holes or notches 30 equidistantly spaced around the bearing 26,28 to provide for passage of fluid through the bearing 26 or 28 and then through the motor 20 and also to provide passage means for stator coil leads 31, 32, 33 and 34. A stainless steel rotor shaft 36 is mounted in and between the bearings 26 and 28 with a distal end portion 38 of the shaft 36 extending outwardly from the motor 20. A rotor 39 of the motor 20 has permanent magnets mounted thereon having opposite pluralities to provide a two pole rotor 39, as shown in FIG. 6.

According to the teachings of the present invention, mounted adjacent the inner surface of the stator housing 22 is a flexible circuit board 40 having mounted thereon four flat stator coil branches 41, 42, 43 and 44 (FIG. 7). The geometry of the stator coil branches 41-44 printed on the flexible circuit board 40 converts a two phase alternating current into a rotating sinusoidal current distribution thereby providing the necessary constant rotation and lower power dissipation required for the motor 20.

At what is typically the proximal end 46 of the motor 20 there is mounted an end cap 48 having slots 50 therethrough through which the leads 31, 32, 33 and 34 can extend and a central passageway 52 therethrough which receives a tube 54 for supplying or withdrawing fluid from inside the motor 20 as shown in FIG. 6. Such fluid can flow through the, the passageway 52 in the end cap 48, the notches 30 in one bearing 28, around the rotor 39 and through the notches 30 in the other bearing 26 when it is desired to deliver fluid to the vessel in which the motor 20 is located.

Alternatively, fluid can be withdrawn from the vessel via these passages to the tube 54 when, for example, a vacuum is placed on the tube 54.

Referring now to FIG. 7 it will be seen that the stator coil branches 41, 42, 43 and 44 are integral with each other in one stator coil formation 60 with a first input lead 31 leading to three legs 61, 62 and 63 of the coil branch 41 of a first frame coil 64, the legs 61-63 being defined between internal notches 65 and 66 which are etched or otherwise formed through a sheet 70 of conductive, e.g., metal or metallic, material from which the coil formation 60 is formed and by a side edge 71 of the sheet 70 and a slot 72 extending from an upper edge 74 of the sheet 70 from which the leads 31–34 extend toward a lower edge 76, but only to a lower margin 78.

The circuit board is made of Kapton ™ and has a thickness of between 0.01 and 0.03 millimeters (mm). The sheet of conductive material is preferably made of copper and has a thickness between 0.01 and 0.03 mm.

The preferred approximate dimensions of the coils and leads are as follows:
Coil lead length: between 1.0 and 10.0 mm.
Coil lead width: between 0.1 and 0.5 mm.
Coil legs width: between 0.02 and 10.0 mm.
Coil width: W (FIG. 7) between 0.5 and 10.0 mm.
Coil length: L (FIG. 8) between 0.1 and 10.0 mm.
Coil formation length: between 0.5 and 50.0 mm.
Coil formation thickness: between 0.02 and 2.0 mm.
Slots and notches width: between 0.02 and 5.0 mm.
Notch length: between 0.1 and 10.0 mm.
Slot length: between 0.1 and 10.0 mm.

In one preferred embodiment, the leads are approximately 0.20 mm wide and approximately 1.70 mm long. The coils are approximately 0.625 mm wide and approximately 1.50 mm long. The slots and notches are approximately 0.050 mm wide. The first and third legs of each coil branch are approximately 0.154 mm wide with the second or middle leg being approximately 0.217 mm. The coil formation 60 has a length of approximately 2.65 mm. The circuit board is approximately 0.015 mm thick and the sheet of conductive material is approximately 0.015 mm thick.

A current $I_0$ flows into the lead 31 through the legs 61–63 of the first coil branch 41 and in and along the lower margin 78 of the coil formation 60 to the third coil branch 43 which is interconnected by the margin 78 to the first coil branch 41 to form the first frame coil 64. The third coil branch 43 is formed with three legs 81, 82 and 83 between two internal notches 84 and 86 and another two slots 88 and 90 which separate the second coil branch 42 from the third coil branch 43 and the third coil branch 43 from the fourth coil branch 44. The three leg coil branch 43 is disposed opposite the first three leg coil branch 41 to form the frame coil 64 when the coil formation 60 is folded into a cylinder.

In like manner, a current $I_1$ goes into the second lead 32 to the second coil branch 42 and through three legs 91, 92 and 93 which are formed between two internal notches 94 and 96 and the slots 72 and 88 which extend to the margin 78. The current $I_1$ will then flow through the margin 78 to the fourth coil branch 44 and then flow through three legs 101, 102 and 103 formed between a side edge 104 of the coil formation 60, the slot 90 and two internal notches 106 and 108 to the lead 34. The second coil branch 42 and the fourth coil branch 44 form a second frame coil 110 which is displaced 90° from the frame coil 64.

The flow of the currents $I_0$ and $I_1$ is shown in more detail in FIGS. 8 and 9.

The current density is approximated to a sinusoidal distribution by splitting the two phase currents into three components, namely $I_{0,1}$ plus $I_{0,2}$ plus $I_{0,3}$ and $I_{1,1}$ plus $I_{1,2}$ plus $I_{1,3}$ as shown in FIG. 8.

In FIG. 9 there is illustrated an equivalent circuit diagram of the stator coil circuits with two current generators $I_1$ and $I_0$. Here the flow of the current $I_1$ and $I_0$ through the stator branch coil 41, 42, 43 and 44 is shown.

The design of the catheter-mounted micro motor 20 and the construction and operation of the frame coils 64 and 110 provide a very small motor without brushes and of minimal complexity which is ideal for the space limitations in blood vessels.

The first and second frame coils combined yields a 2-pole, 2-phase synchronous motor with a permanent magnetic rotor.

Because of the extremely small dimensions involved, the rotor 39 is preferably a composite magnet (an imbedded polymer sold by the company Kinetron at Tilburg, The Netherlands).

The synchronous motor principle requires for two magnetic poles and a set of two frame coil pairs where each coil produces a current density profile of a sinusoidal nature along the circumference.

This is achieved with the frame coils 64 and 110 where, in each frame coil, the number of conductors along the circumference varies as a sinus function.

By using a flexprint design, it is possible to achieve a sinusoidal current density by the use of standard size conductors but varying the pitch, This yields a discrete approximation of the sinus curve.

Due to the limited diameter of small micro motors, a single-layer flexprint is the preferred construction since it requires an overall thickness of 15 $\mu$m Cu+15 $\mu$m Kapton ™. This requires each coil branch to extend only over $\frac{1}{4}$ of the circumference.

The sinus curve now has to be approximated over the angle range of $1/4 \pi$ to $3/4 \pi$ instead of 0 to $\pi$. The contribution of the areas $0-\frac{1}{4}\pi$ and $3/4\pi-\pi$ is minimal.

Using the total area yields:

$$\int_0^\pi \sin x\, dx = 2$$

or for power leaving out the areas $0-\frac{1}{4}\pi$ and $3/4\pi-\pi$ yields:

$$\int_0^\pi \sin^2 x\, dx = \tfrac{1}{2}\pi$$

$$\int_{\frac{1}{4}\pi}^{\frac{3}{4}\pi} \sin x\, dx = \sqrt{2}$$

or for power $$\int_{\frac{1}{4}\pi}^{\frac{3}{4}\pi} \sin^2 x\, dx = \tfrac{1}{4}\pi + \tfrac{1}{2}$$

1. Using the total area yields:

$$\int_0^\pi \sin x\, dx = 2\ [100\%]$$

2. Using one quadrant yields:

$$\int_{\frac{1}{4}\pi}^{\frac{3}{4}\pi} \sin x\, dx = 1.41\ [71\%]$$

3. Considering power as in 1. yields:

$$\int_{-0}^{\pi} \sin^2 x\, dx = 1.57\ [100\%]$$

4. Using one quadrant as in 1. yields:

$$\int_{\frac{1}{4}\pi}^{\frac{3}{4}\pi} \sin^2 x\, dx = 1.29\ [82\%]$$

These considerations of power and current density lead to the design of the coil branches 41–44 with the central conductor or middle leg 62, 92, 82 and 102 of each coil branch 41–44 being given a value of 100% current density and the side conductors or side legs 61, 65, 91, 93, 81, 83, 101, and 103 then being 71% ($\frac{1}{2}\sqrt{2}$) of the current density in the middle leg.

It will be appreciated that it is difficult to provide true frame coils with the single-layer printed circuit since the crossing of conductors is not possible. Furthermore a wire bridge would be too bulky and very hard to implement.

For this reason, the separate coil branches 41–44 are all interconnected at one side. This can only work if the sum of all incoming currents is zero. Hence a balanced current source must be used for each of the two phases.

Figure 10:
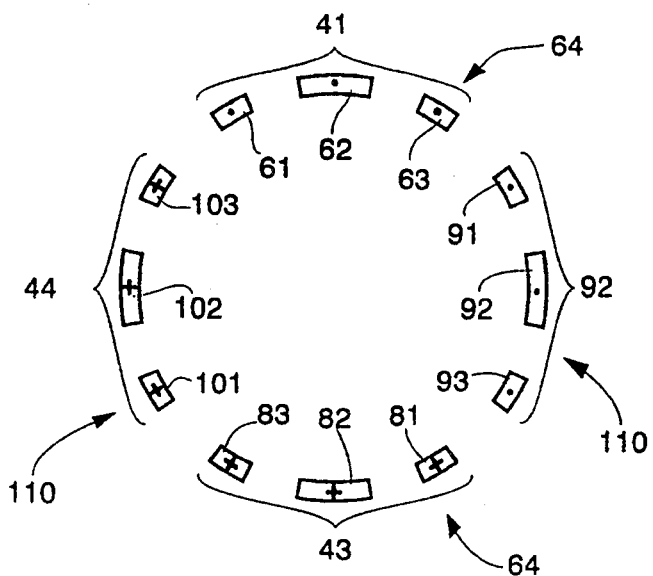
FIG. 10 is a mechanical schematic diagram of a cross-section of the two coil stator frame coils each including first and second branches with each branch having three legs one with the dots representing the current going in at the beginning of a first sinusoidal A.C. current entering the first branch of a first frame coil and of a second sinusoidal A.C. current entering the first branch of a second frame coil and the pluses indicating the first current coming out of the second branch of the first frame coil and the second current coming out of the second branch of the second frame coil.

FIG. 10 shows the arrangement of the coil branches 41 and 43 to form the frame coil 64 and the arrangement of the coil branches 42 and 44 to form the second frame coil 110. Also, there is shown the direction of the current flowing through the coil branches 41–44 at the beginning of the application of the two phases of current which are 90° out of phase from each other.

Figure 11:
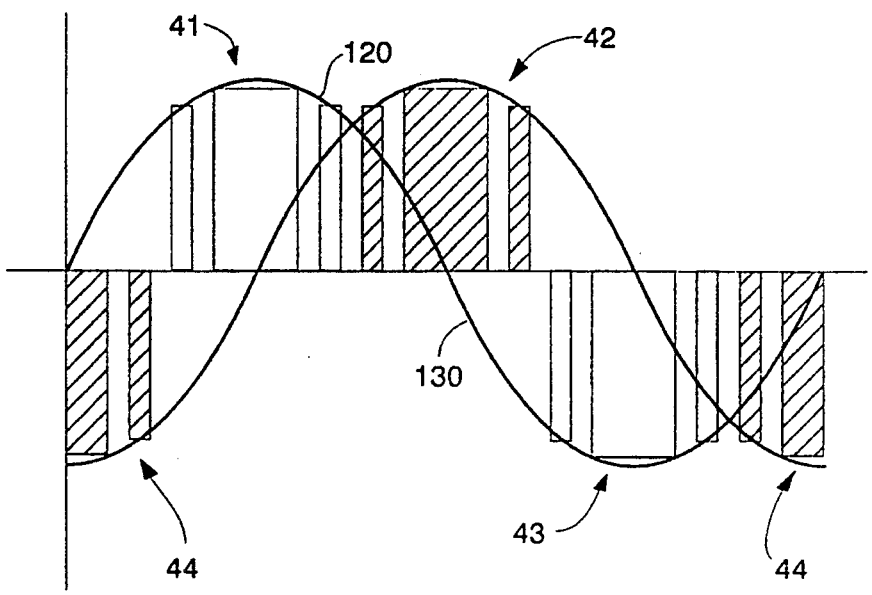
FIG. 11 is a graph of the two phase sinusoidal current waves that are supplied to the two frame coils and through the two branches of each coil with the first phase entering the first branch of the first coil and then exiting out of the second branch of the first coil and the second phase entering the first branch of the second coil and exiting the second branch of the second coil and shows the mechanical effect of the configuration of the branches of the coils affecting the current density such that the effective current density from the three legs of each branch of each coil is represented by rectangles in FIG. 11.

Then, in FIG. 11 there is illustrated the application of the sinusoidal two phase currents 120 and 130 with the phase current 130 being 90° out of phase from the phase current 120. The current density in the motor, as a result of these two sinusoidal currents 120 and 130, out of phase by 90°, as affected by the mechanical construction and arrangement of the coil branches 41–44, and particularly the legs thereof, results in effective current densities in the form of pulses of current through each leg of each coil branch 41–44 of the two frame coils 64 and 110, as shown by the rectangles in FIG. 11.

The combined effect of these effective coil densities (the rectangles in FIG. 11) is a generally sinusoidal, almost square, wave of electromagnetic force. This generally sinusoidal wave of electromagnetic force has few harmonics when compared to ideal two phase motors and, in particular, less second harmonics. Furthermore, as demonstrated by the formulas set forth above, a very high power output of 82% is obtained with the micro motor 20 of the present invention having stator coil branches 41–44 for two frame coils 64 and 110 formed on a printed circuit board.

From the foregoing description it will be apparent that the instrument 1', 1" or 1''' and the micro motor 20 of the present invention have a number of advantages, some of which have been described above and others of which are inherent in the invention. Accordingly, the scope of the invention is only to be limited as necessitated by the accompanying claims.

We claim:

1. A disposable intra-luminal catheter probe type ultrasonic instrument for the examination and/or treatment of blood vessels having a small transverse cross-section, said instrument including a catheter comprising a body and a tip having a distal end and a distal end portion adapted to be introduced into a lumen of a blood vessel and a proximal portion, said catheter having a diameter no greater than 3 millimeters, a rotatable member mounted for rotation in said tip and having a rotatable acoustical mirror face, and a micro motor in said tip having a length no greater than 6 millimeters and a diameter no greater than 2.4 millimeters and being coupled to said rotatable member for rotating said rotatable member at a selected rpm, and means for generating and supplying sound waves to said mirror face of said rotatable member.

2. The instrument of claim 1 wherein said motor has a side which faces toward said distal end and includes a drive shaft on said side facing said distal end, and said rotatable mirror face lies in a plane that intersects at an angle the axis of the drive shaft and the axis of the propagation of sound waves from said means for generating sound waves.

3. The instrument of claim 2 wherein said means for generating sound waves comprises a transducer mounted in said tip facing said mirror face and having a central passageway therethrough through which said drive shaft extends.

4. The instrument of claim 1 wherein said motor is mounted in said distal end portion and includes a drive shaft extending rearwardly from said distal end, said rotatable member is mounted to said drive shaft, said acoustic mirror face lies in a plane which intersects at an angle the axis of said drive shaft and the axis of said propagation of sound waves from said means for generating sound waves and said means for generating sound waves is positioned in said tip opposite said mirror face.

5. The instrument of claim 1 wherein said motor has a length no greater than approximately 4 millimeters and a diameter no greater than approximately 1 millimeter.

6. The instrument of claim 1 wherein said motor is operated at a speed of rotation synchronized with a raster across a visual display to which the echoes of the sound waves received by the mirror are supplied and the rotation of the acoustic mirror is oriented with respect to the raster.

7. The instrument of claim 1 wherein said catheter includes electrical conductors for supplying electric power to said motor and to said sound wave generating means.

8. The instrument of claim 1 wherein said catheter has a central channel that also extends through said sound wave generating means and said shaft through and to said distal end of said tip distal portion.

9. The instrument of claim 8 including a flexible guidewire which is extendable through said central channel.

10. The instrument of claim 1 wherein said means for generating sound waves are constructed and arranged to generate sound waves at a frequency no greater than 60 megahertz.

11. The instrument of claim 1 wherein said means for generating sound waves are constructed and arranged to generate sound waves at a frequency of between approximately 15 and 45 megahertz.

12. The instrument of claim 1 wherein said means for generating sound waves are constructed and arranged to generate sound waves at a frequency of approximately 30 megahertz to obtain a sufficient depth of field with sufficient resolution to determine the makeup or constitution of the matter, such as tissue or plaque, in the space being investigated around the catheter tip.

13. A method for examining a blood vessel using a disposable intra-luminal ultrasonic instrument including a catheter having an elongate axis and a hollow distal end portion, said method comprising the steps of:
mounting, for rotation in the distal end portion of the catheter, an acoustical mirror face;
positioning said acoustical mirror face at an angle to the elongate axis of the catheter;
mounting a transducer in the distal end portion of the catheter in a position to propagate acoustic waves toward the acoustical mirror face;
constructing a micromotor having a length no greater than approximately 6 millimeters and a diameter no greater than approximately 2.4 millimeters;
mounting the micromotor in the distal end portion of the catheter;
connecting the micromotor to the acoustical mirror face; and,
energizing the micromotor to rotate the acoustical mirror face while at the same time energizing the transducer to produce and supply sound waves to the rotating acoustical mirror face.

14. A disposable intra-luminal ultrasonic instrument comprising: a catheter having an elongate axis and a hollow distal end portion;
an acoustical mirror face;
means for mounting said acoustical mirror face for rotation in said distal end portion of the catheter with said acoustical mirror face arranged at an angle to said elongate axis of the catheter;
a transducer;
means for mounting said transducer in said distal end portion of said catheter in a position to propagate acoustic waves toward said catheter in a position to propagate acoustic waves toward said acoustical mirror face;
a micromotor having a length no greater than approximately 6 millimeters and a diameter no greater than approximately 2.4 millimeters;
means for mounting said micromotor in said distal end portion of said catheter;
means for connecting said micromotor to said acoustical mirror face;
means for connecting said micromotor to a source of energy for energizing said micromotor to rotate said acoustical mirror face; and,
means for connecting said transducer to a source of energy for energizing said transducer to produce and supply sound waves to said rotatable acoustical mirror face.

15. A disposable intra-luminal instrument ultrasonic instrument for insertion into a blood vessels having a small transverse cross-section, said instrument comprising an elongate including a body having a distal end and a distal end portion adapted to be introduced into a lumen of a blood vessel and a proximal portion, said body having a diameter no greater than 3 millimeters, a rotatable member mounted for rotation in said distal end portion and having a rotatable acoustical mirror face, a micro motor in said distal end portion having a length no greater than 6 millimeters and a diameter no greater than 2.4 millimeters and being coupled to said rotatable member for rotating said rotatable member at a selected rpm, and means for generating and supplying sound waves to said mirror face of said rotatable member.

16. A method for examining a blood vessel using a disposable intra-luminal ultrasonic instrument comprising an elongate body having an elongate axis and including a hollow distal end portion, said method comprising the steps of:
mounting, for rotation in the distal end portion of the elongate body, an acoustical mirror face;
positioning said acoustical mirror face at an angle to the elongate axis of the elongate body;
mounting a transducer in the distal end portion of the elongate body in a position to propagate acoustic waves toward the acoustical mirror face;
constructing a micromotor having a length no greater than approximately 6 millimeters and a diameter no greater than approximately 2.4 millimeters;
mounting the micromotor in the distal end portion of the elongate body;
connecting the micromotor to the acoustical mirror face; and, energizing the micromotor to rotate the acoustical mirror face while at the same time energizing the transducer to produce and supply sound waves to the rotating acoustical mirror face.

17. A disposable intra-luminal ultrasonic instrument comprising: a elongate body having an elongate axis and including a hollow distal end portion;
an acoustical mirror face;
means for mounting said acoustical mirror face for rotation in said distal end portion of said elongate body with said acoustical mirror face arranged at an angle to said elongate axis of said elongate body;
a transducer;
means for mounting said transducer in said distal end portion of said elongate body in a position to propagate acoustic waves toward said acoustical mirror face;
a micromotor having a length no greater than approximately 6 millimeters and a diameter no greater than approximately 2.4 millimeters;
means for mounting said micromotor in said distal end portion of said elongate body;
means for connecting said micromotor to said acoustical mirror face;
means for connecting said micromotor to a source of energy for energizing said micromotor to rotate said acoustical mirror face; and,
means for connecting said transducer to a source of energy for energizing said transducer to produce and supply sound waves to said rotatable acoustical mirror face.

18. A disposable ultrasonic instrument for the examination of blood vessels or for the treatment of blood vessels or for the guiding of an interventional device through blood vessels and similar lumina having a small transverse cross-section, said instrument comprising a distal end portion and being adapted to be introduced into a lumen, said distal end portion having a diameter no greater than 3 millimeters, a rotatable member in said distal end portion, a micro motor in said distal end portion having a length no greater than 6 millimeters and a diameter no greater than 2.4 millimeters and being coupled to said rotatable member for rotating said rotatable member at a selected rpm, and means for generating and supplying sound waves to said mirror face of said rotatable member.

* * * * *